US012725676B2

(12) United States Patent
Zhang et al.

(10) Patent No.: US 12,725,676 B2
(45) Date of Patent: Sep. 1, 2026

(54) DNA MATRIX PROCESSING METHOD BASED ON COMBINED RESTRICTION DIGESTION MECHANISM

(71) Applicant: Dalian University, Dalian City (CN)

(72) Inventors: Qiang Zhang, Dalian City (CN); Shihua Zhou, Dalian City (CN); Shaoxia Xu, Dalian City (CN); Yinan Hu, Dalian City (CN); Bin Wang, Dalian City (CN)

(73) Assignee: DALIAN UNIVERSITY, Dalian (CN)

( * ) Notice: Subject to any disclaimer, the term of this patent is extended or adjusted under 35 U.S.C. 154(b) by 1229 days.

(21) Appl. No.: 17/677,356

(22) Filed: Feb. 22, 2022

(65) Prior Publication Data

US 2023/0132150 A1 Apr. 27, 2023

(30) Foreign Application Priority Data

Oct. 26, 2021 (CN) ......................... 202111250188.1

(51) Int. Cl.

| | |
|---|---|
| ***G16B 5/10*** | (2019.01) |
| ***C12N 15/10*** | (2006.01) |
| ***G16B 50/30*** | (2019.01) |

(52) U.S. Cl.

CPC ........... *G16B 5/10* (2019.02); *C12N 15/1093* (2013.01); *G16B 50/30* (2019.02)

(58) Field of Classification Search

CPC ....... G16B 5/10; G16B 50/30; C12N 15/1093

See application file for complete search history.

(56) References Cited

PUBLICATIONS

Zhixin Zhou, Jianbang Wang, R. D. Levine, Francoise Remacle, Itamar Willner; Chem. Sci., Mar. 17, 2021, 12, 5473-5483. (Year: 2021).*

Xinyi Sun, Xuedong Zheng, Sue Zhao, Yuan Liu, Bin Wang; RSC Adv., Feb. 24, 2020, 10, 7956-7966 (Year: 2020).*

* cited by examiner

*Primary Examiner* — Olivia M. Wise
*Assistant Examiner* — Emilie A Smith
(74) *Attorney, Agent, or Firm* — Yuhao Liang

(57) ABSTRACT

The present disclosure discloses a DNA matrix processing method based on a combined restriction digestion mechanism, including the following steps: constructing a single auxiliary strand-mediated combined restriction digestion mechanism; introducing an auxiliary strand based on the single auxiliary strand-mediated combined restriction digestion mechanism, to obtain a dual auxiliary strands-mediated combined restriction digestion mechanism; and constructing DNA matrix processing and a weighted sum of Boolean matrix multiplication with the dual auxiliary strands-mediated combined restriction digestion mechanism; in which the two auxiliary strands are directly used as elements involved in the matrix processing, and the 2N auxiliary strands are combined into $N^2$ four-pronged restriction digestion structures in the presence of E6 type DNAzymes to cleave $N^2$ substrate strands. Meanwhile, due to high-efficiency catalysis and specific recognition, the E6 type DNAzymes make the matrix processing rapid and accurate.

6 Claims, 9 Drawing Sheets

$$\begin{bmatrix} M_{11} & M_{12} \\ M_{21} & M_{22} \end{bmatrix} \begin{bmatrix} X_{11} \\ X_{21} \end{bmatrix} = \begin{bmatrix} M_{11}X_{11}+M_{12}X_{21} \\ M_{21}X_{11}+M_{22}X_{21} \end{bmatrix} = \begin{bmatrix} F1 \\ F2 \end{bmatrix}$$

FIG. 5

DNA MATRIX PROCESSING METHOD BASED ON COMBINED RESTRICTION DIGESTION MECHANISM

CROSS REFERENCE TO RELATED APPLICATION

This patent application claims the benefit and priority of Chinese Patent Application No. 202111250188.1 filed on Oct. 26, 2021, the disclosure of which is incorporated by reference herein in its entirety as part of the present application.

TECHNICAL FIELD

The present disclosure relates to the technical field of DNA matrix processing, specifically to a DNA matrix processing method based on a combined restriction digestion mechanism.

BACKGROUND ART

In recent years, many complex DNA-based computing systems have been implemented using different bioengineering methods. For example, Zhou et al., using graphene oxide combined with DNA, constructed a novel digital comparison system capable of comparing two or more binary numbers. Later, Zhou et al. built for the first time a cube root logic circuit for calculation of ten-digit binary numbers (within a decimal number of 1000). This research offers new insights into complex computing circuits and demonstrates outstanding capabilities of DNA in the field of biological computing. FAN et al. designed a DNA-based switching circuit using a DNA strand replacement technology to implement digital calculations, providing a novel strategy for the development of molecular computers.

In addition, half adder and half subtractor, full adder and full subtractor, encoder and decoder, and quadratic root calculation and neuron calculation models are emerging in endlessly. In particular, Qian and Winfree et al. proposed a "seesaw gate" DNA motif based on the DNA strand replacement technology. Later, on this basis, a 4-neuron Hopfield neural network calculation model and a winner-takes-all neural network model were further constructed to realize the "heart guessing" technique. This is a breakthrough research in the molecular intelligent computing realm.

In fact, the neural network calculation consists of only a few operations, including matrix processing. However, in the matrix processing, the calculation is mainly achieved by DNA strand replacement. This method is simple and rapid, but will also cause slow leakages at the same time, affecting the accuracy of processing results. Therefore, there is a need to find a novel way to construct matrix processing operations. The matrix processing performance directly affects the performance of the entire computing system. Therefore, it is necessary to conduct research on the matrix processing.

SUMMARY

An objective of the present disclosure is to provide a DNA matrix processing method based on a combined restriction digestion mechanism. The method makes the matrix processing rapid and accurate, reduces cross-interference between DNA strands, and improves the stability of the matrix processing.

To achieve the above objective, the present disclosure provides a DNA matrix processing method based on a combined restriction digestion mechanism, including the following steps:

constructing a single auxiliary strand-mediated combined restriction digestion mechanism;

introducing an auxiliary strand based on the single auxiliary strand-mediated combined restriction digestion mechanism, to obtain a dual auxiliary strands-mediated combined restriction digestion mechanism; and constructing DNA matrix processing and a weighted sum of Boolean matrix multiplication with the dual auxiliary strands-mediated combined restriction digestion mechanism.

In some embodiments, the single auxiliary strand-mediated combined restriction digestion mechanism includes an auxiliary strand Aux, an E6 type DNAzyme DZ3 and a substrate BrA3T; the auxiliary strand Aux is an input signal of the mechanism, and a fluorescence released by a cleaved substrate is an output signal of the mechanism.

In some embodiments, the dual auxiliary strands-mediated combined restriction digestion mechanism includes two auxiliary strands Aux1-z11 and Aux2-z11, an E6 type DNAzyme DE3 and a substrate ErA3T; the two auxiliary strands Aux1-z11 and Aux2-z11 are an input signal of the mechanism, and a fluorescence released by a cleaved substrate is an output signal of the mechanism.

In some embodiments, the DNA matrix processing multiply a matrix M and a matrix X, specifically including: using one auxiliary strand as an element in the matrix M and another auxiliary strand as an element in the matrix X, and subjecting the element in the matrix M to multiplication by the element in the matrix X; under action of a reporting module, conducting transduction on a multiplication result successfully to a fluorescence signal, and determining the multiplication result by reading the fluorescence signal.

In some embodiments, the reporting module includes an E6 type DNAzyme E1, an E6 type DNAzyme E2 and two functionalized substrate strands R1 and R2.

In some embodiments, a matrix M and a matrix X are input for the weighted sum of the Boolean matrix multiplication, weights are E6 type DNAzymes E1 and E2, and two functionalized substrate strands R1' and R2' are used to detect an output signal; in weighted sum processing of the Boolean matrix multiplication, an element in an i-th row and a j-th column of an output matrix F are equal to a product of an element in an i-th row of the matrix M and a corresponding element in a j-th column of the matrix X, multiplied by a sum of respective weights of the matrix M and the matrix X.

In some embodiments, the two auxiliary strands, as two input signals of the dual auxiliary strands-mediated combined restriction digestion mechanism, are added into a digestion reaction system in an equal proportion simultaneously.

In some embodiments, DNA strands of the matrix M and the matrix X, as matrix elements involved in the processing, are added into a reaction system of the DNA matrix processing in an equal proportion simultaneously.

Due to the above technical solutions, the embodiments of present disclosure may achieve the following technical effects: the two auxiliary strands are directly used as elements involved in the matrix processing, and the 2N auxiliary strands are combined into $N^2$ four-pronged restriction digestion structures in the presence of the E6 type DNAzymes to cleave $N^2$ substrate strands. Meanwhile, due to high-efficiency catalysis and specific recognition, the E6 type DNAzymes make the matrix processing rapid and accurate. In addition, each auxiliary strand only combines with the corresponding E6 type DNAzyme, thereby reducing the cross-interference between DNA strands to improve the stability of the matrix processing. The dual auxiliary strands-mediated combined restriction digestion mechanism qualitatively and quantitatively processes the Boolean matrix multiplication; the DNA matrix processing method designed in the present disclosure lays a foundation for constructing a more complex and larger processing platform, and shows great potentials in large-scale information processing systems.

BRIEF DESCRIPTION OF THE DRAWINGS

FIG. 5 shows a schematic diagram of multiplication of the matrix M and the matrix X;

DETAILED DESCRIPTION OF THE EMBODIMENTS

The technical solution in the examples of the present disclosure is now described clearly and completely with reference to the accompanying drawings for examples of the present disclosure. It will be understood that the described examples are merely a part of, rather than all, embodiments of the present disclosure. All other embodiments derived from the examples of the present disclosure by those skilled in the art without creative work shall fall within the protection scope of the present disclosure.

Figure 1:
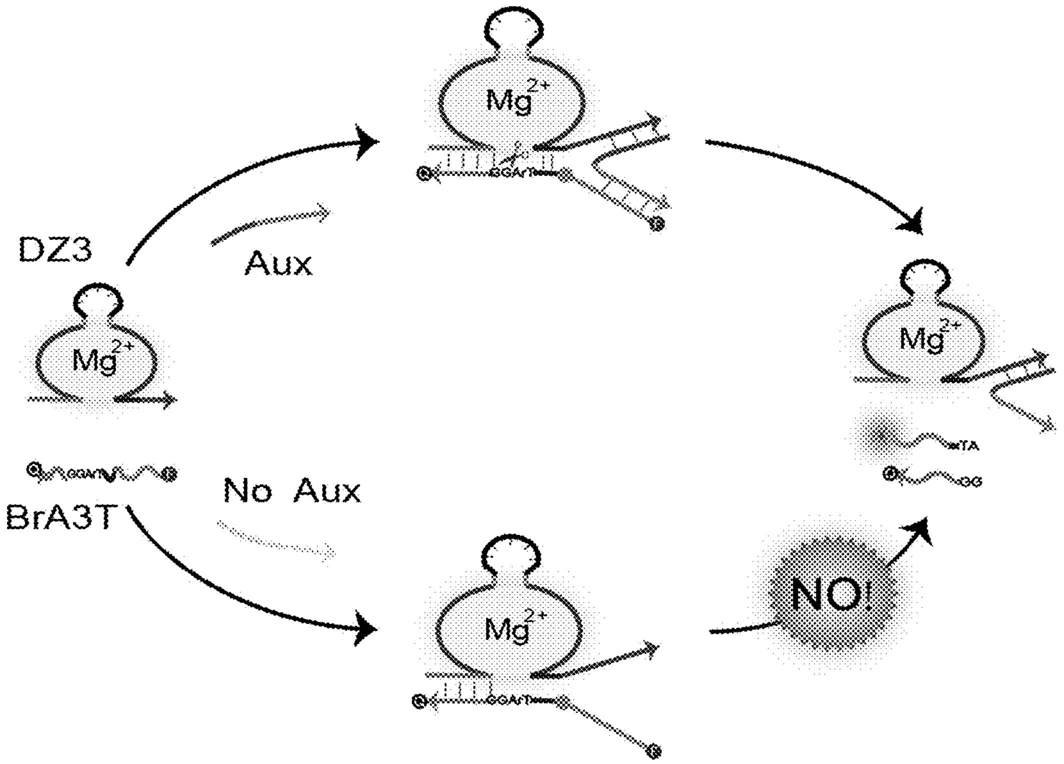
FIG. 1 shows a schematic diagram of a process of the single auxiliary strand-mediated combined restriction digestion mechanism.
Figure 2:
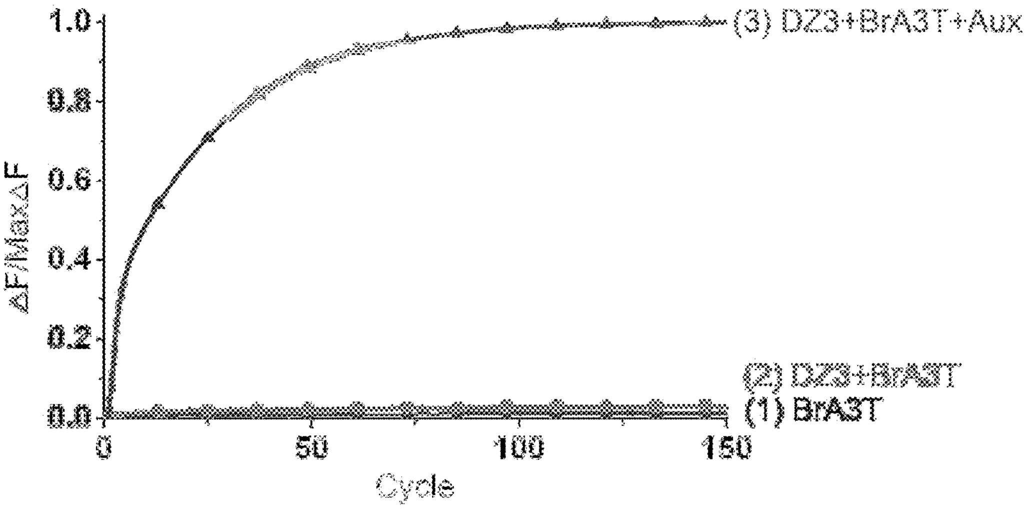
FIG. 2 shows a normalized fluorescence curve of the single auxiliary strand-mediated combined restriction digestion mechanism.

A single auxiliary strand-mediated combined restriction digestion mechanism is constructed as shown in FIG. 1. An E6 type DNAzyme DZ3 cleaves a substrate BrA3T only when an auxiliary strand Aux is input, to generate an output signal. FIG. 2 is a fluorescence curve of this mechanism, verifying that a fluorescence signal is generated only when there is an input.

Figure 3:
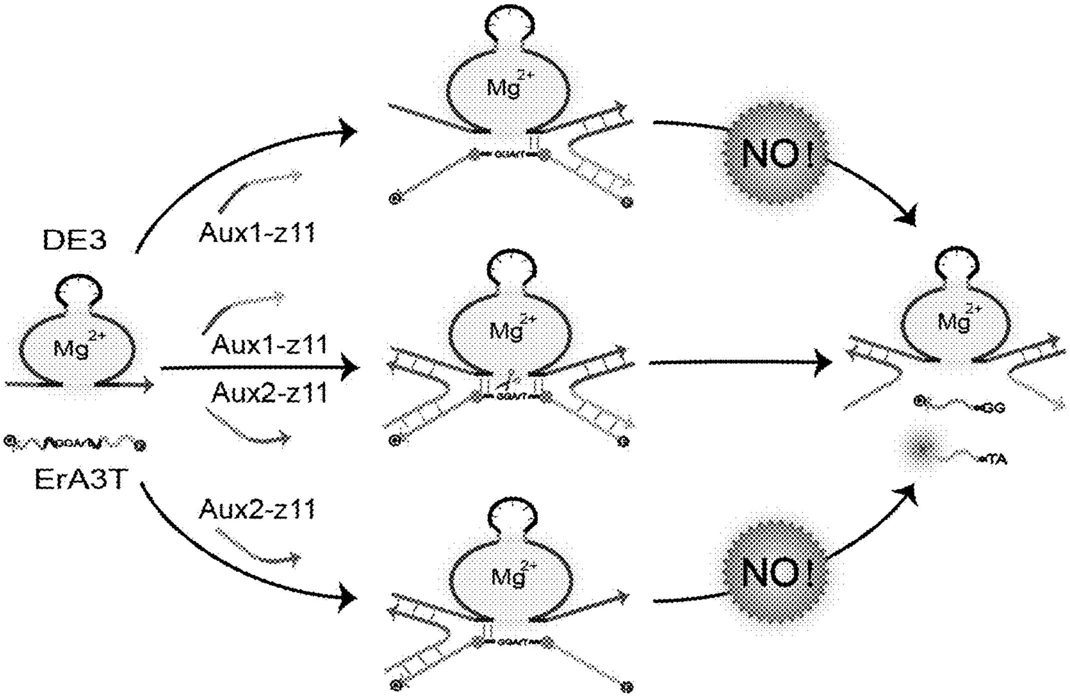
FIG. 3 shows a schematic diagram of a process of the dual auxiliary strands-mediated combined restriction digestion mechanism.
Figure 4:
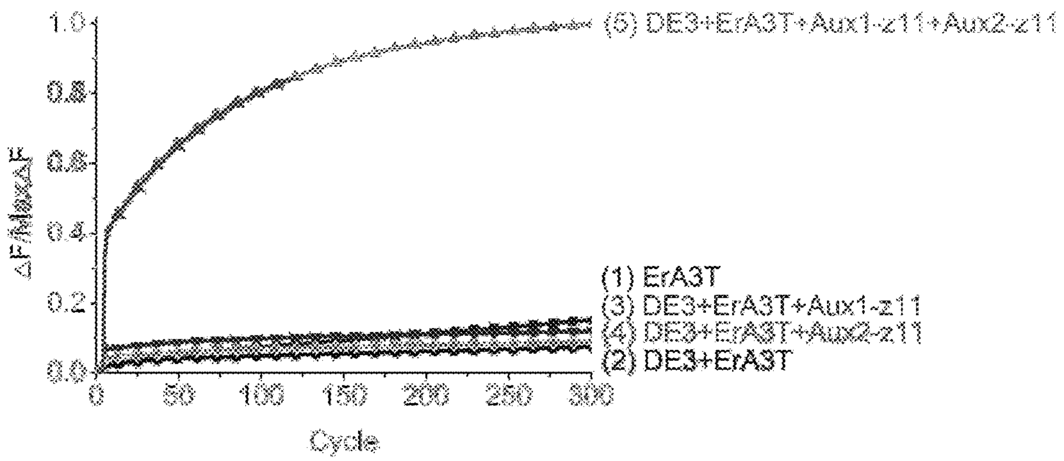
FIG. 4 shows a normalized fluorescence curve of the dual auxiliary strands-mediated combined restriction digestion mechanism.

A dual auxiliary strands-mediated combined restriction digestion mechanism is constructed as shown in FIG. 3. An E6 type DNAzyme DE3 cleaves a substrate ErA3T only when two auxiliary strands Aux1-z11 and Aux2-z11 are input, to generate an output signal. FIG. 4 is a fluorescence curve of this mechanism, proving that a fluorescence signal is generated only when the two auxiliary strands are each input.

Figure 6:
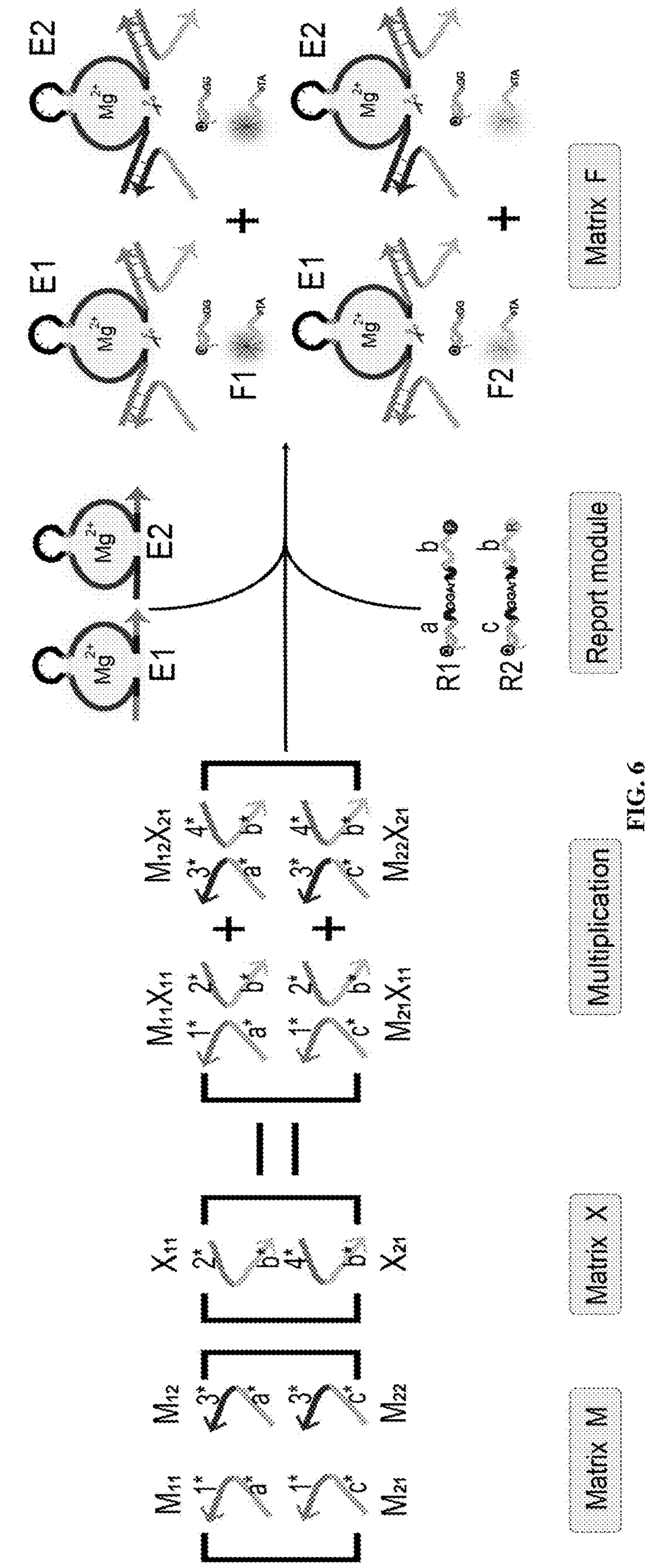
FIG. 6 shows a schematic diagram of a process of multiplying the matrix M by the matrix X.
Figure 7:
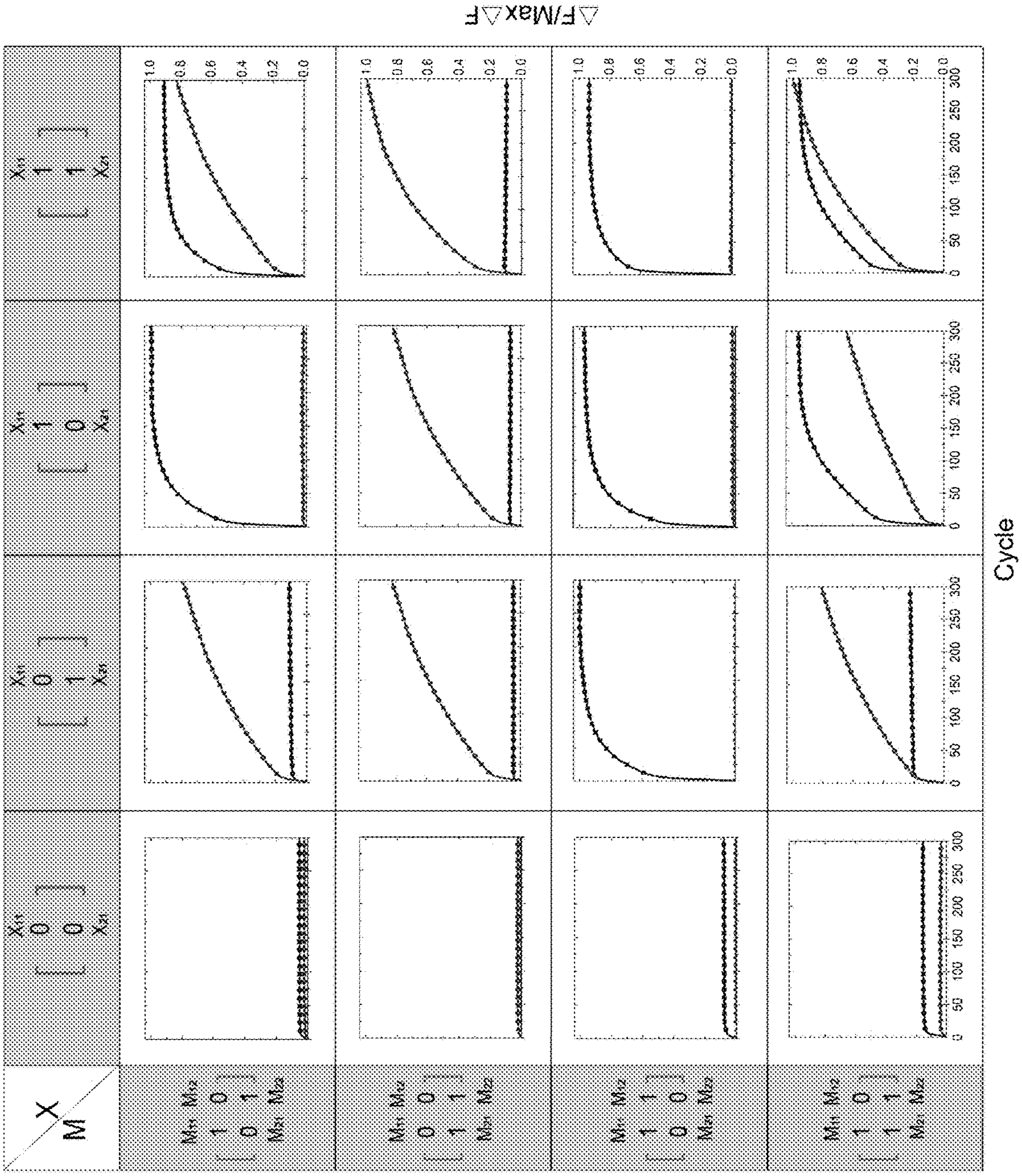
FIG. 7 shows a fluorescence curve of 4 different M matrices multiplied by 4 different X matrices.

DNA matrix processing was achieved by the dual auxiliary strands-mediated combined restriction digestion mechanism; FIG. 5 is a schematic diagram of multiplication of two matrices. FIG. 6 shows a demonstration process of multiplying two matrices using DNA, where the matrix M is a 2×2 matrix, including the first row of elements $M_{11}$ and $M_{12}$, and the second row of elements $M_{21}$ and $M_{22}$; and the matrix X includes two elements $X_{11}$ and $X_{21}$. A reporting module includes E6 type DNAzymes E1 and E2 and two functionalized substrate strands R1 and R2, where in the R1, a 5'-end modifies a fluorophore FAM, and a 3'-end modifies a quenching group BHQ1; in the R2, a 5'-end modifies a fluorophore ROX, and a 3'-end modifies a quenching group BHQ2. The elements $M_{11}$ and $M_{12}$ in the first row of the matrix M are multiplied by the two elements $X_{11}$ and $X_{21}$ of the matrix X to obtain two combinations $M_{11}X_{11}$ and $M_{12}X_{21}$. These two combinations each perform an "AND" operation, that is, if any element is missing in the combination, a processing result of the combination is "0". The $M_{11}X_{11}$ combines with the E6 type DNAzyme E1 to form a combined restriction digestion mechanism, which cleaves the substrate R1 to generate a fluorescence signal. The $M_{12}X_{21}$ combines with the E6 type DNAzyme E2, and to cleave the substrate R1, producing a same fluorescence signal. The two combinations $M_{11}X_{11}$ and $M_{12}X_{21}$ perform an "OR" operation, that is, when any one or both of the combinations exist, a processing result is "1", otherwise it is "0". Secondly, the elements $M_{21}$ and $M_{22}$ in the second row of the matrix M are multiplied by the two elements $X_{11}$ and $X_{21}$ of the matrix X, to obtain two combinations $M_{21}X_{11}$ and $M_{22}X_{21}$. Similarly, the two elements of each combination perform an "AND" operation, and the two elements are indispensable; otherwise, a processing result of the combination is "0". The $M_{21}X_{11}$ combines with the E6 type DNAzyme E1 to cleave a fluorogenic substrate R2 to generate a fluorescence signal. The $M_{22}X_{21}$ combines with the E6 type DNAzyme E2 to cleave the substrate R2 to produce a same fluorescence signal. The "OR" operation is performed between the two combinations. When there is one or both combinations, a processing result is "1", otherwise it is "0". FIG. 7 shows a fluorescence curve of 4 different M matrices multiplied by 4 different X matrices. The matrix element "1" means that the input strand represented by the position exists; and the matrix element "0" means that the input strand represented by the position does not exist. The obtained processing result is defined by whether the fluorescence signal rises or not. If the fluorescence signal rises, it means the processing result is "1", and if the fluorescence signal does not rise, it means the processing result is "0".

Figure 8:
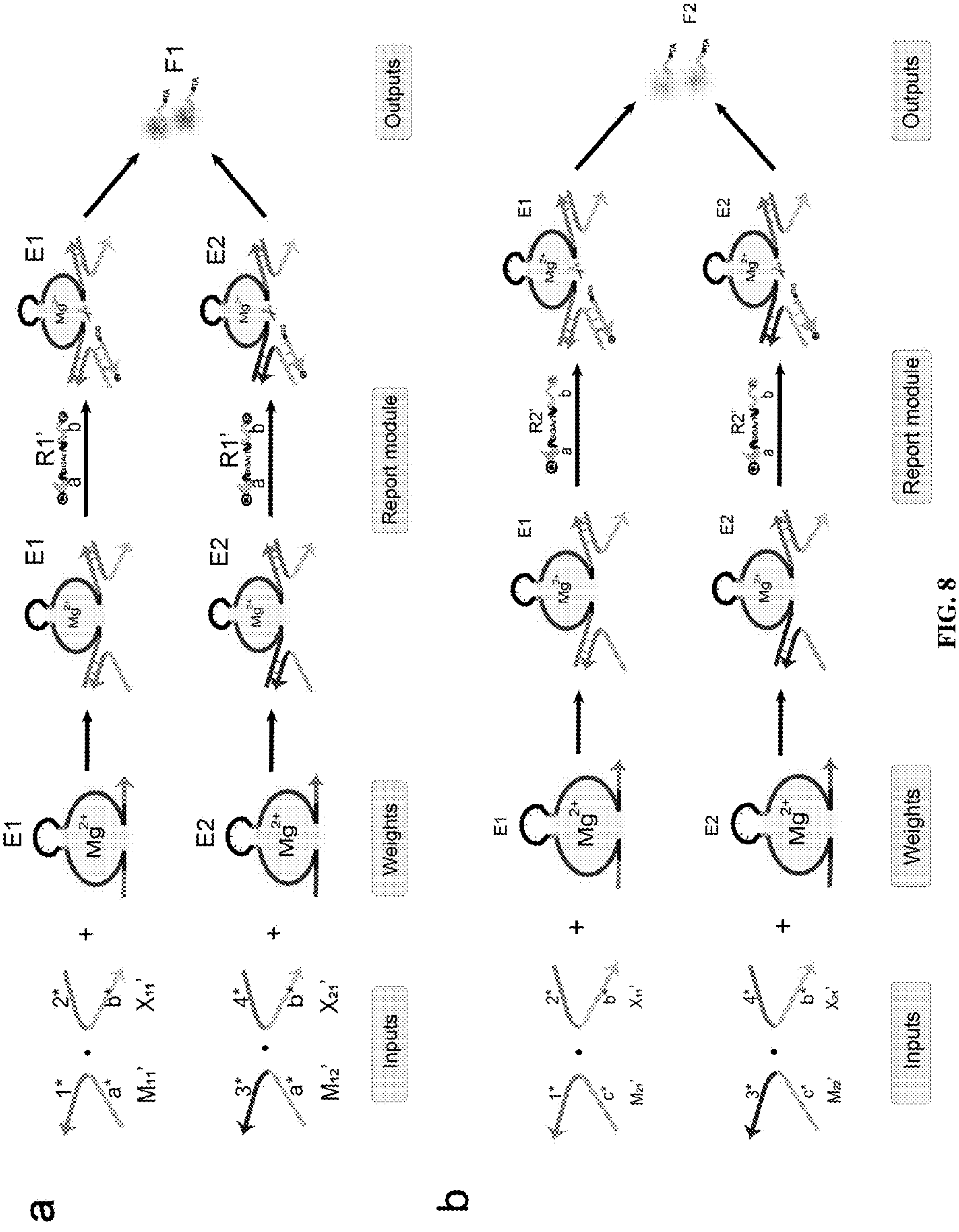
FIG. 8 shows a schematic diagram of a process of a weighted sum of the matrix M multiplied by the matrix X; in which a is a weighted sum of an element value F1 in a first row of an output matrix F, and b is a weighted sum of an element value F2 in a second row of the output matrix F.
Figure 9:
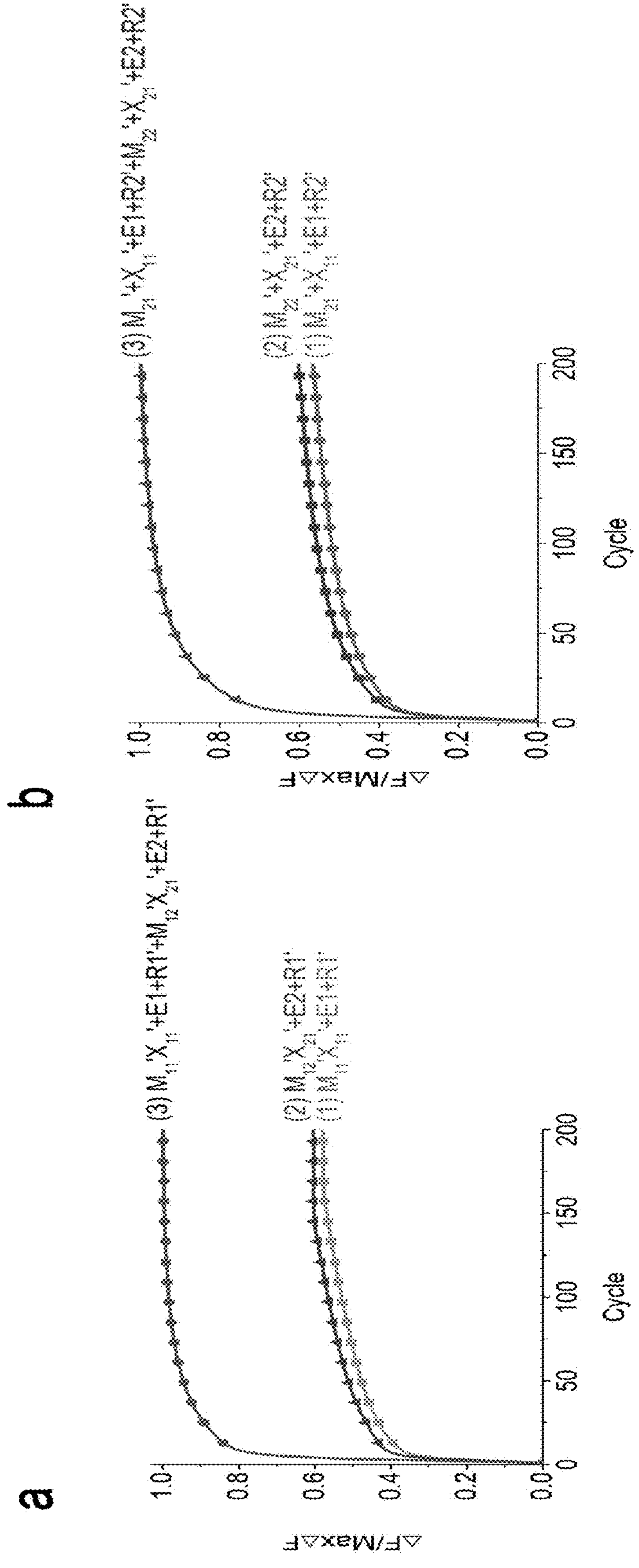
FIG. 9 is a fluorescence curve of the weighted sum of the matrix M and the matrix X; in which a is a fluorescence curve of the F1, and b is a fluorescence curve of the F2.

The dual auxiliary strands-mediated combined restriction digestion mechanism realizes a weighted sum of Boolean matrix multiplication. In this experiment, a fixed weight is set to 1, and an output signal depends on an input of the matrix element. A in FIG. 8 shows a schematic diagram of a weighted sum of an element F1 in the first row of an output matrix F. An input auxiliary strand combination is multiplied by respective weights to form the dual auxiliary strands-mediated combined restriction digestion mechanism, to cleave a same substrate to release the fluorescence signal. A rationality of the weighted sum processing the F1 is verified using a fluorescence quantitative experiment. As shown in a of FIG. 9, when only a combination $M_{11}'X_{11}'$ is input, the combination is multiplied by a weight E1, to cleave a substrate R1' to generate a fluorescence signal that reaches a level; when only a combination $M_{12}'X_{21}'$ is input, the combination is multiplied by a weight E2, to also cleave the substrate R1' to generate a fluorescence signal that reaches a level; when the two combinations $M_{11}'X_{11}'$ and $M_{12}'X_{21}'$ are both input, the combination $M_{11}'X_{11}'$ is multiplied by the weight E1 and the combination $M_{12}'X_{21}'$ is multiplied by the weight E2, to form two types of dual auxiliary strands-mediated combined restriction digestion structures. Meanwhile, the substrate R1' is cleaved to produce the same fluorescence signal, and a fluorescence value reaches a higher level, realizing summing A schematic diagram of summation of the element F2 in the second row of the matrix F is shown in b of FIG. 8, and a summation method is the same as that of the F1. B in FIG. 9 is a fluorescence curve of summation of the F2.

Example 1

DNA matrix processing was constructed specifically as follows:

(1) E6 type DNAzymes E1 and E2 and two functionalized substrate strands R1 and R2 were mixed at a ratio of 1:1 in a 1×TAE/$Mg^{2+}$ buffer to form a reporting module;

(2) elements of corresponding matrix M and matrix X were added as input strands to the reporting module obtained in step (1) according to a Boolean matrix to be processed, with a concentration of 0.3 μM, and reaction was conducted at 25° C. for approximately 20 h. After being added, the input was combined with corresponding E6 type DNAzyme and substrate in the reporting module to form a combined restriction digestion mechanism, to cut the substrate to generate a fluorescence signal. If the fluorescence signal rose, it indicated that a processing result of the corresponding elements of the two matrices was "1"; and if the fluorescence signal did not rise, it indicated that the processing result of the corresponding elements of the two matrices was "0".

Example 2

A weighted sum of Boolean matrix multiplication (taking F1 as an example) was constructed specifically as follows:

(1) an E6 type DNAzyme E1 and a functionalized substrate strand R1' were mixed at a ratio of 1:2 in a 1×TAE/$Mg^{2+}$ buffer, and placed in a test tube 1;

(2) an E6 type DNAzyme E2 and the functionalized substrate strand R1' were mixed at a ratio of 1:2 in the 1×TAE/$Mg^{2+}$ buffer, and placed in a test tube 2;

(3) the E6 type DNAzymes E1 and E2 and the functionalized substrate strand R1' were mixed in a ratio of 1:1:2 in the 1×TAE/$Mg^{2+}$ buffer, and placed in a test tube 3;

(4) input strands $M_{11}'$ and $X_{11}'$ were added to the test tube 1, at a concentration of 0.3 μM, and reaction was conducted at 25° C. for approximately 20 h;

(5) input strands $M_{12}'$ and $X_{21}'$ were added to the test tube 2, at a concentration of 0.3 μM, and reaction was conducted at 25° C. for approximately 20 h; and (6) input strands $M_{11}'X_{11}'$ and $M_{12}'X_{21}'$ were added to the test tube 3, at a concentration of 0.3 μM, and reaction was conducted at 25° C. for approximately 20 h; the results of the fluorescence experiment were shown in a of FIG. 9, verifying the success of the weighted sum module.

The above are merely descriptions of preferred embodiments, but are not intended to limit of the present disclosure. It should be noted that many modifications and variations can be made by those of ordinary skill in the art without departing from the technical principle of the present disclosure. These modifications and variations should also be deemed as falling within the protection scope of the present disclosure.

What is claimed is:

1. A DNA matrix processing method based on a combined restriction digestion mechanism, comprising the following steps:

constructing a single auxiliary strand-mediated combined restriction digestion mechanism; wherein the single auxiliary strand-mediated combined restriction digestion mechanism comprises an auxiliary strand Aux, an E6 type DNAzyme DZ3 and a substrate BrA3T; the auxiliary strand Aux is an input signal of the mechanism, and a fluorescence released by a cleaved substrate is an output signal of the mechanism;

introducing an auxiliary strand based on the single auxiliary strand-mediated combined restriction digestion mechanism, to obtain a dual auxiliary strands-mediated combined restriction digestion mechanism; wherein the dual auxiliary strands-mediated combined restriction digestion mechanism comprises two auxiliary strands Aux1-z11 and Aux2-z11, an E6 type DNAzyme DE3 and a substrate ErA3T; the two auxiliary strands Aux1-z11 and Aux2-z11 are an input signal of the mechanism, and a fluorescence released by a cleaved substrate is an output signal of the mechanism; and constructing DNA matrix processing and a weighted sum of Boolean matrix multiplication with the dual auxiliary strands-mediated combined restriction digestion mechanism.

2. The method according to claim 1, wherein the DNA matrix processing multiplies a matrix M and a matrix X, specifically comprising: using one auxiliary strand as an element in the matrix M and another auxiliary strand as an element in the matrix X, and subjecting the element in the matrix M to multiplication by the element in the matrix X; under the action of a reporting module, conducting transduction on a multiplication result successfully to a fluorescence signal, and determining the multiplication result by reading the fluorescence signal.

3. The method according to claim 2, wherein the reporting module comprises an E6 type DNAzyme E1, an E6 type DNAzyme E2 and two functionalized substrate strands R1 and R2.

4. The method according to claim 1, wherein a matrix M and a matrix X are input for the weighted sum of the Boolean matrix multiplication, weights are E6 type DNAzymes E1 and E2, and two functionalized substrate strands R1' and R2' are used to detect an output signal; in weighted sum processing of the Boolean matrix multiplication, an element in an i-th row and a j-th column of an output matrix F is equal to a product of an element in an i-th row of the matrix M and a corresponding element in a j-th column of the matrix X, multiplied by a sum of respective weights of the matrix M and the matrix X.

5. The method according to claim 1, wherein the two auxiliary strands, as two input signals of the dual auxiliary strands-mediated combined restriction digestion mechanism, are added into a digestion reaction system in an equal proportion simultaneously.

6. The method according to claim 1, wherein DNA strands of the matrix M and the matrix X, as matrix elements involved in the processing, are added into a reaction system of the DNA matrix processing in an equal proportion simultaneously.

* * * * *